(12) United States Patent
Fu

(10) Patent No.: US 9,907,915 B2
(45) Date of Patent: Mar. 6, 2018

(54) PIN HEAD STRUCTURE OF SAFETY SYRINGE

(71) Applicant: Vantex Biotechnology Co., Ltd., Tortola (VG)

(72) Inventor: Meng-Chen Fu, Taipe (TW)

(73) Assignee: Vantex Biotechnology Co., Ltd. (VG)

( * ) Notice: Subject to any disclaimer, the term of this patent is extended or adjusted under 35 U.S.C. 154(b) by 680 days.

(21) Appl. No.: 14/504,314

(22) Filed: Oct. 1, 2014

(65) Prior Publication Data
US 2016/0095982 A1  Apr. 7, 2016

(51) Int. Cl.
*A61M 5/32* (2006.01)

(52) U.S. Cl.
CPC ......... *A61M 5/3243* (2013.01); *A61M 5/3271* (2013.01)

(58) Field of Classification Search
CPC .............. A61M 5/3243; A61M 5/3271; A61M 2005/3253; A61M 5/3245
See application file for complete search history.

(56) References Cited

U.S. PATENT DOCUMENTS

| | | | |
|---|---|---|---|
| 8,888,713 B2 * | 11/2014 | Crawford | A61B 5/1422 600/576 |
| 2004/0210197 A1 * | 10/2004 | Conway | A61B 5/150351 604/198 |
| 2006/0178639 A1 * | 8/2006 | Eric | A61M 5/3243 604/192 |
| 2008/0177235 A1 * | 7/2008 | DiBiasi | A61M 5/326 604/192 |
| 2009/0326477 A1 * | 12/2009 | Liversidge | A61M 5/326 604/198 |
| 2010/0087785 A1 * | 4/2010 | Tschirren | A61M 5/2448 604/208 |
| 2013/0218090 A1 * | 8/2013 | Roberts | A61M 5/326 604/192 |
| 2013/0281939 A1 * | 10/2013 | Roberts | A61M 5/326 604/198 |
| 2013/0324886 A1 * | 12/2013 | Fu | A61B 5/150549 600/576 |
| 2014/0210197 A1 * | 7/2014 | Girard | B60P 3/226 280/837 |
| 2014/0236095 A1 * | 8/2014 | Slemmen | A61M 5/326 604/198 |
| 2014/0303564 A1 * | 10/2014 | Roberts | A61M 5/326 604/198 |
| 2016/0082201 A1 * | 3/2016 | Stillman | A61M 5/46 604/117 |

* cited by examiner

*Primary Examiner* — Rebecca E Eisenberg

(57) ABSTRACT

A needle head structure of a safety syringe includes a protecting cover, a first sleeve, a second sleeve, a syringe holder and a plunger. The first sleeve, second sleeve and syringe holder are structures with mutually latched embedding protrusion and latch portion. The plunger includes a guide channel, and is operated with the syringe holder to reduce a remaining liquid. The first sleeve, second sleeve and syringe holder are latched with one another to fix an end of the syringe holder. After the use of the syringe, a first sleeve is pulled towards a an end to link the second sleeve, so that the first sleeve is latched to an end of the second sleeve, and the other end of the second sleeve is fixed to the syringe holder, so as to provide a convenient operation to users and reduce the risk of being pierced by the needle head structure accidentally.

7 Claims, 15 Drawing Sheets

PIN HEAD STRUCTURE OF SAFETY SYRINGE

FIELD OF THE INVENTION

The present invention relates to a needle head structure of a safety syringe, and more particularly to the needle head structure having two tubular bodies latched to one another to protect and keep a syringe body from being exposed to the outside.

BACKGROUND OF THE INVENTION

To reduce the risk and danger of being pierced by a needle head of a syringe accidentally and protect us by separating the needle head, a "safety syringe" as disclosed in R.O.C. Pat. No. M339311 adopts a combination of a sleeve and a telescopic tube, wherein a sliding groove is formed at the external periphery of the sleeve and a combining groove is concavely formed at the sleeve, and the telescopic tube comprises an elastic member, a sliding pipe with an embedding hole, and a pushing member, and the elastic member is configured to be corresponsive to the combining groove, and the sliding pipe is installed outside the sleeve, so that the tubes are sheathed and configured to be corresponsive to the elastic member, and a fixing member and a bump are provided to users to pull and rotate the telescopic tube to fix and hold the sleeve in order to protect the syringe body and preventing it from being exposed to the outside.

In addition, a "disposable safety syringe covering apparatus" as disclosed in R.O.C. Pat. No. 595482 comprises a cylindrical base unit and a sleeve unit, and the cylindrical base unit has a protrusion, and the sleeve unit has a T-shaped sliding groove, and the front end of the sleeve unit has an opening, wherein the cylindrical base unit is sheathed on an end of a needle to sheath the sleeve on the cylindrical base unit, so that the sleeve may slide back and forth along the longitudinal sliding groove, and the transverse sliding groove is fixed, so as to constitute a telescopic syringe covering apparatus.

The aforementioned two patented inventions are provided for protecting used needle heads to reduce the risk of being pierced by the needle head accidentally. Since these prior arts constitute various types of structures and apply the method of rotating the transverse sliding groove to fix the sleeve or cylindrical base unit, but they also increase the risk of loosening components. Therefore, the present invention provides another needle head structure of a safety syringe that improves the safety and secured connection of the needle head structure that are latched by a pulling and positioning method, so as to provide a more convenient use to medical professionals.

SUMMARY OF THE INVENTION

Therefore, it is a primary objective of the present invention to provide a needle head structure with a syringe holder comprising a latch plate with an embedding protrusion, and the latch plate is configured to be corresponsive to a second sleeve.

Another objective of the present invention is to provide a needle head structure with the second sleeve comprising a guide portion, a latch portion and an embedding protrusion, and an end of the needle head structure is configured to be corresponsive to the syringe holder, and the other end of the needle head structure is configured to be corresponsive to the first sleeve.

A further objective of the present invention is to provide a needle head structure with the first sleeve comprising a guide portion, a latch portion and a holding portion, and an end of the needle head structure is configured to be corresponsive to the second sleeve.

Another objective of the present invention is to provide a needle head structure with a protecting cover configured to be corresponsive to an end of the syringe holder.

The technical characteristics of the present invention will become apparent from the following detailed description of a preferred embodiment with reference to the accompanying drawings.

DESCRIPTION OF THE PREFERRED EMBODIMENTS

Figure 1:
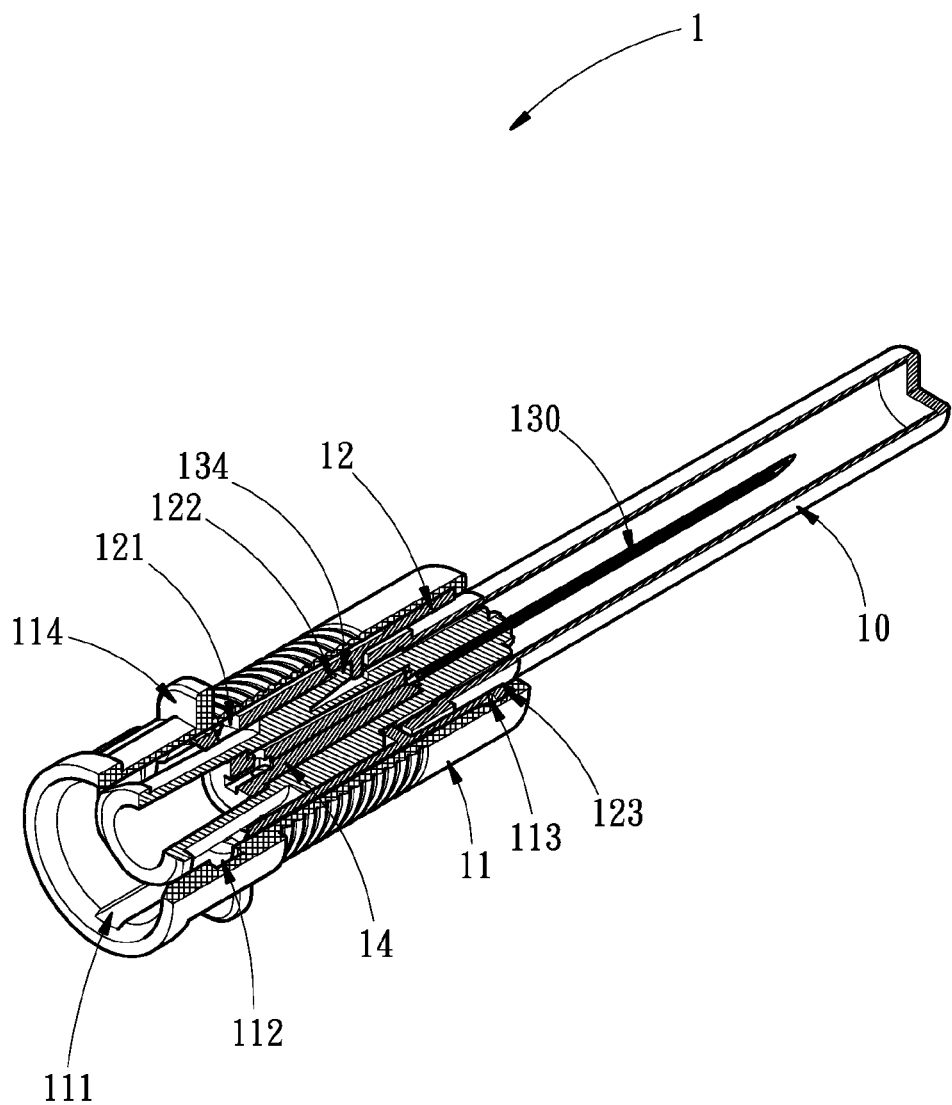
FIG. 1 is a perspective view of a needle head structure of a safety syringe in accordance with the present invention.
Figure 2:
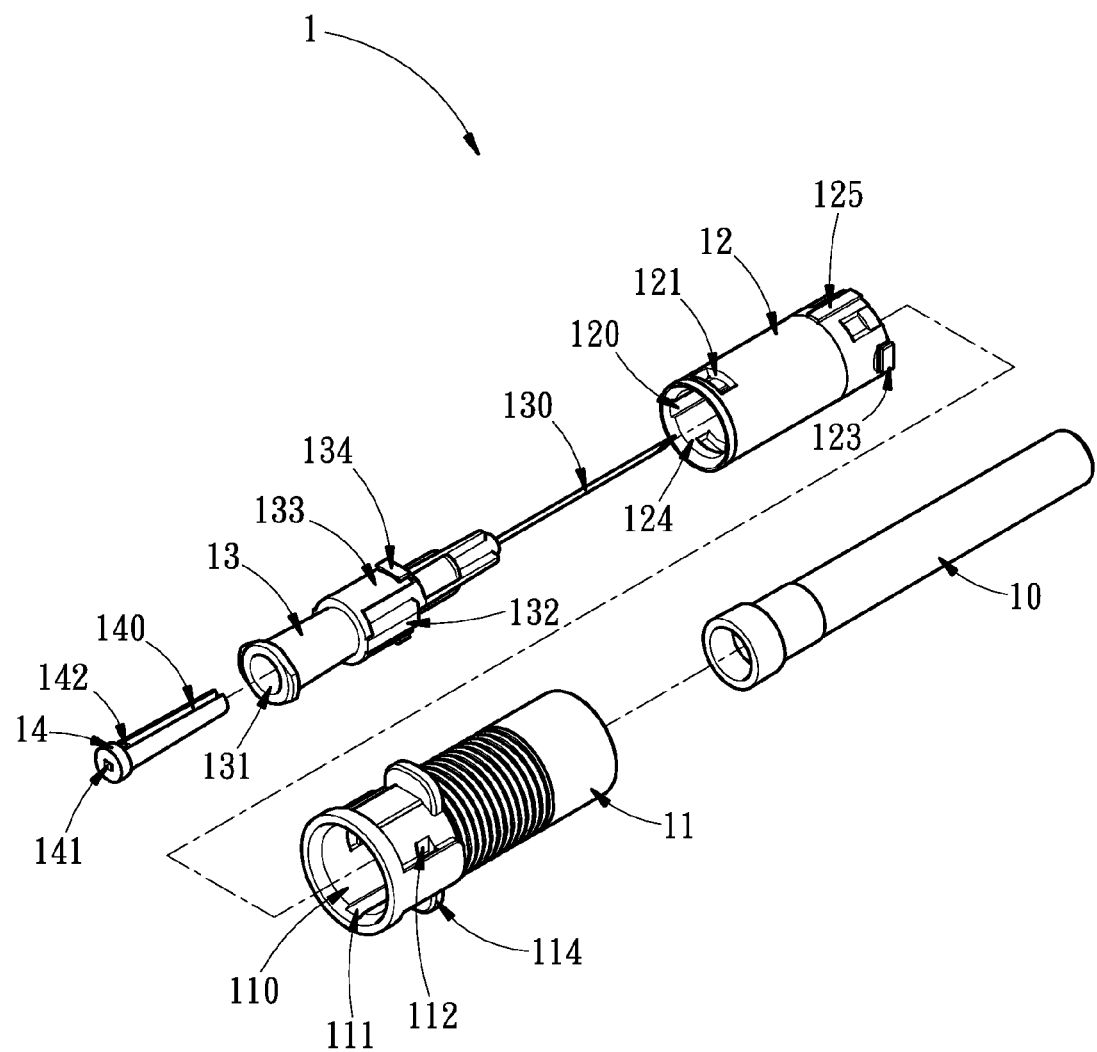
FIG. 2 is an exploded view of a needle head structure of a safety syringe in accordance with the present invention.

With reference to FIGS. 1 and 2 for a needle head structure of a safety syringe in accordance with the present invention, the needle head structure 1 comprises a protecting cover 10, a first sleeve 11, a second sleeve 12, a syringe holder 13 and a plunger 14, wherein the protecting cover 10 is a tubular body having an end opening sheathed on an end of the syringe holder 13.

The first sleeve 11 is a tubular body with an end opening formed at both ends of the first sleeve 11 separately, and having a containing portion 110 formed therein, and the internal periphery of the containing portion 110 includes a longitudinal guide portion 111, a transverse groove 113, and a latch portion 112, and the external periphery of the first sleeve 11 includes a holding portion 114, wherein the guide portion 111 is configured to be corresponsive to the positioning portion 125 of the second sleeve 12, and the groove 113 and the latch portion 112 are provided for accommodating and installing an embedding protrusion 123 of the second sleeve 12.

The second sleeve 12 is a tubular body having two end openings, a containing portion 124 formed therein, and a longitudinal groove 122, a latch portion 121 and a transverse guide portion 120 formed at the internal periphery of the containing portion 124, wherein the groove 122 and the latch portion 121 are provided for accommodating and fixing the embedding protrusion 134 of the latch plate 133 of the syringe holder 13, and the guide portion 120 is configured corresponsive to the positioning portion 132 of the syringe holder 13.

The syringe holder 13 has a containing portion 131 disposed at an end, and a base of a syringe body 130 disposed at the other end, a latch plate 133 with the corresponding embedding protrusion 134 longitudinally formed at the external periphery of the syringe holder 13, and a positioning portion 132 transversely formed at the external periphery of the syringe holder 13. Wherein, the embedding protrusion 134 of the latch plate 133 is configured to be corresponsive to the groove 122 and the latch portion 121 of the second sleeve 12, and the positioning portion 132 is configured to be corresponsive to the guide portion 120 of the second sleeve 12.

The plunger 14 is substantially in the shape of an umbrella, and includes a diversion portion 140, an injecting portion 141 and a diversion hole 142, and the diameter of the periphery of the plunger 14 is equal to the diameter of the internal periphery of the containing portion 131 of the syringe holder 13. The plunger 14 is provided for guiding a liquid, retarding the flow, and reducing the liquid remained.

With the structures of the plunger 14, syringe holder 13, second sleeve 12 and first sleeve 11, a safety syringe 1 is formed. The corresponding first sleeve 11 and second sleeve 12 are provided for protecting the syringe body 130 and preventing the syringe body 130 from being exposed to the outside.

Figure 3:
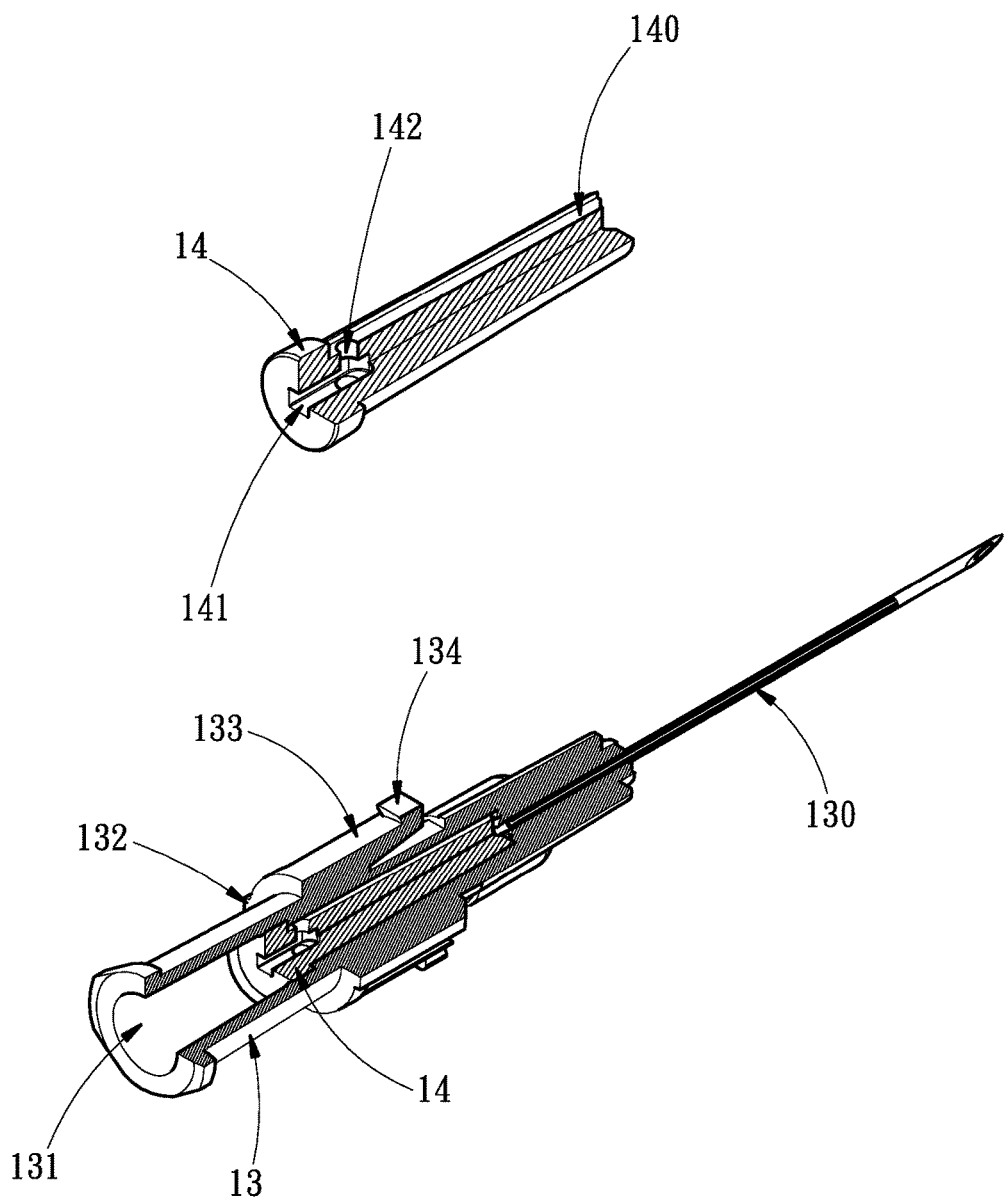
FIG. 3 is a schematic view of a plunger and a syringe holder of a needle head structure of a safety syringe in accordance with the present invention.
Figure 4:
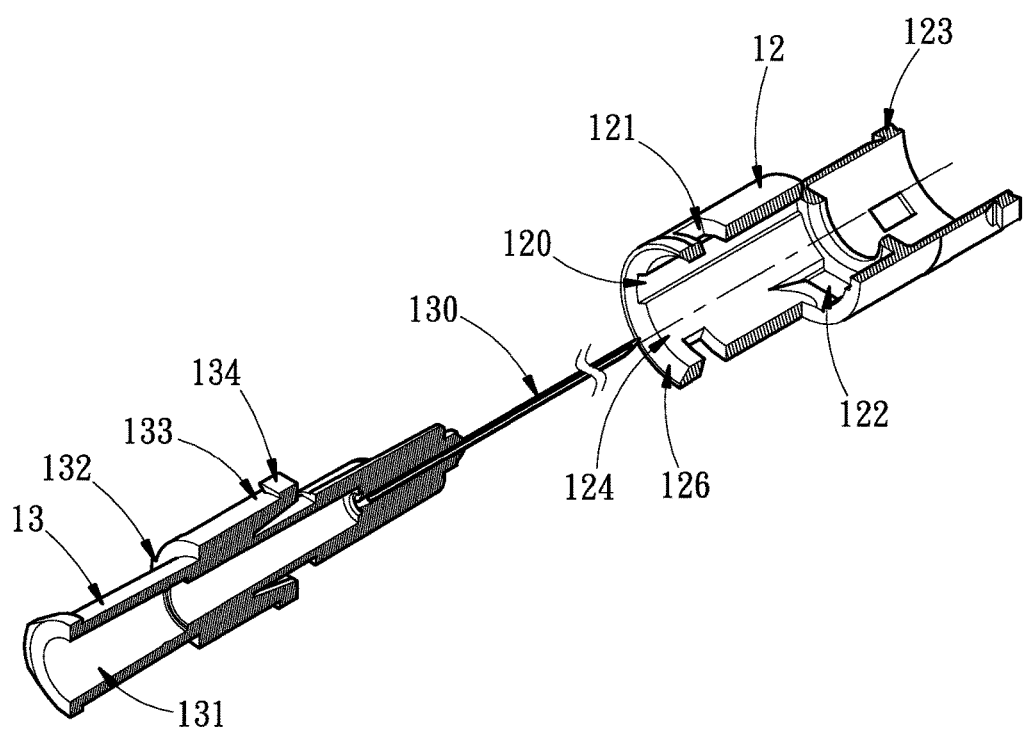
FIG. 4 is a schematic view of a syringe holder and a second sleeve of a needle head structure of a safety syringe in accordance with the present invention.

In FIG. 3, the plunger 14 is installed in the containing portion 131 of the syringe holder 13. Since the plunger 14 has a diversion portion 140, an injecting portion 141 and a diversion hole 142, the injected liquid is guided from the injecting portion 141 to the diversion hole 142, and then guided form the diversion portion 140 to the syringe body 130 and the liquid is injected into a patient's subcutaneous tissues, and the plunger 14 has the effect of reducing the flow and remains, so that medicine contained in the liquid may be injected completely.

Figure 5A:
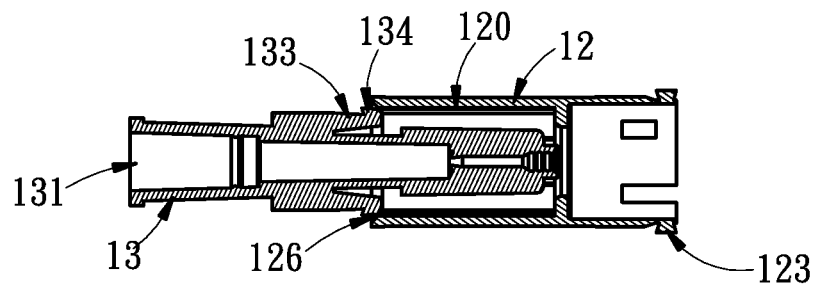
FIGS. 5a~5d are front views of installing a syringe holder and a second sleeve of a needle head structure of a safety syringe in accordance with the present invention.
Figure 5B:
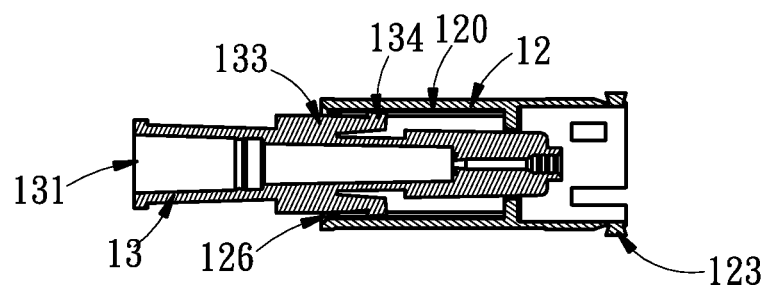
Figure 5C:
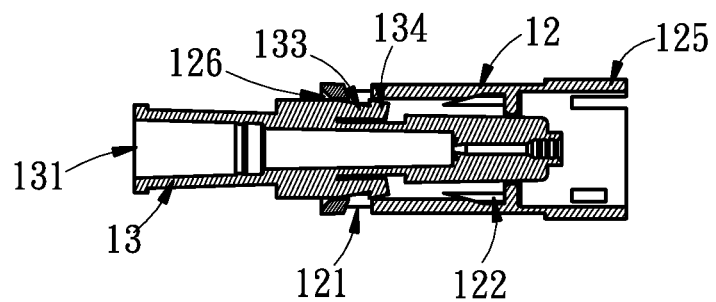
Figure 5D:
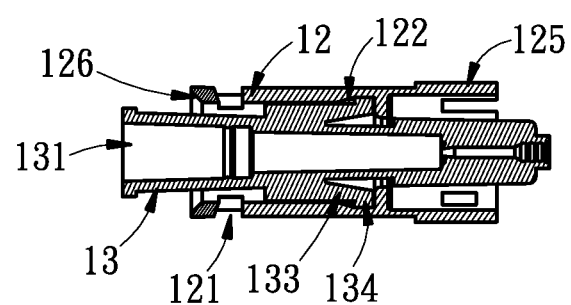
Figure 5E:
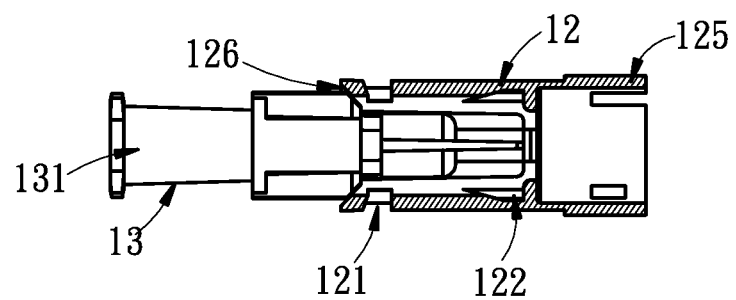
FIGS. 5e~5h are top views of installing a syringe holder and a second sleeve of a needle head structure of a safety syringe in accordance with the present invention.
Figure 5F:
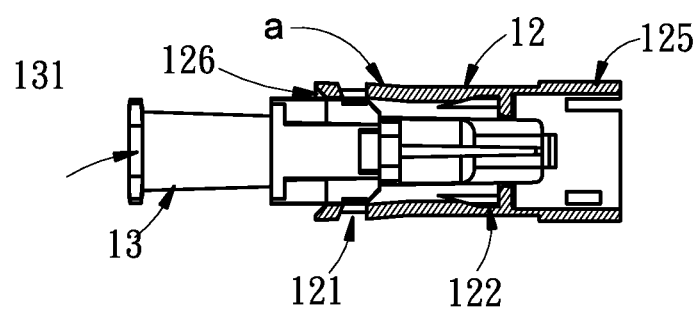
Figure 5G:
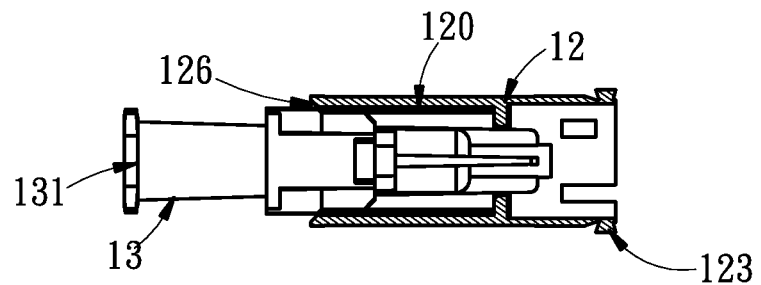
Figure 5H:
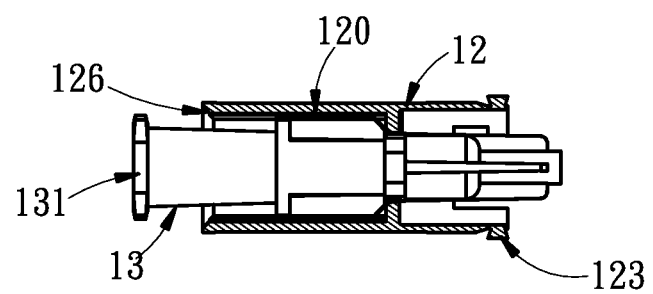
Figure 6:
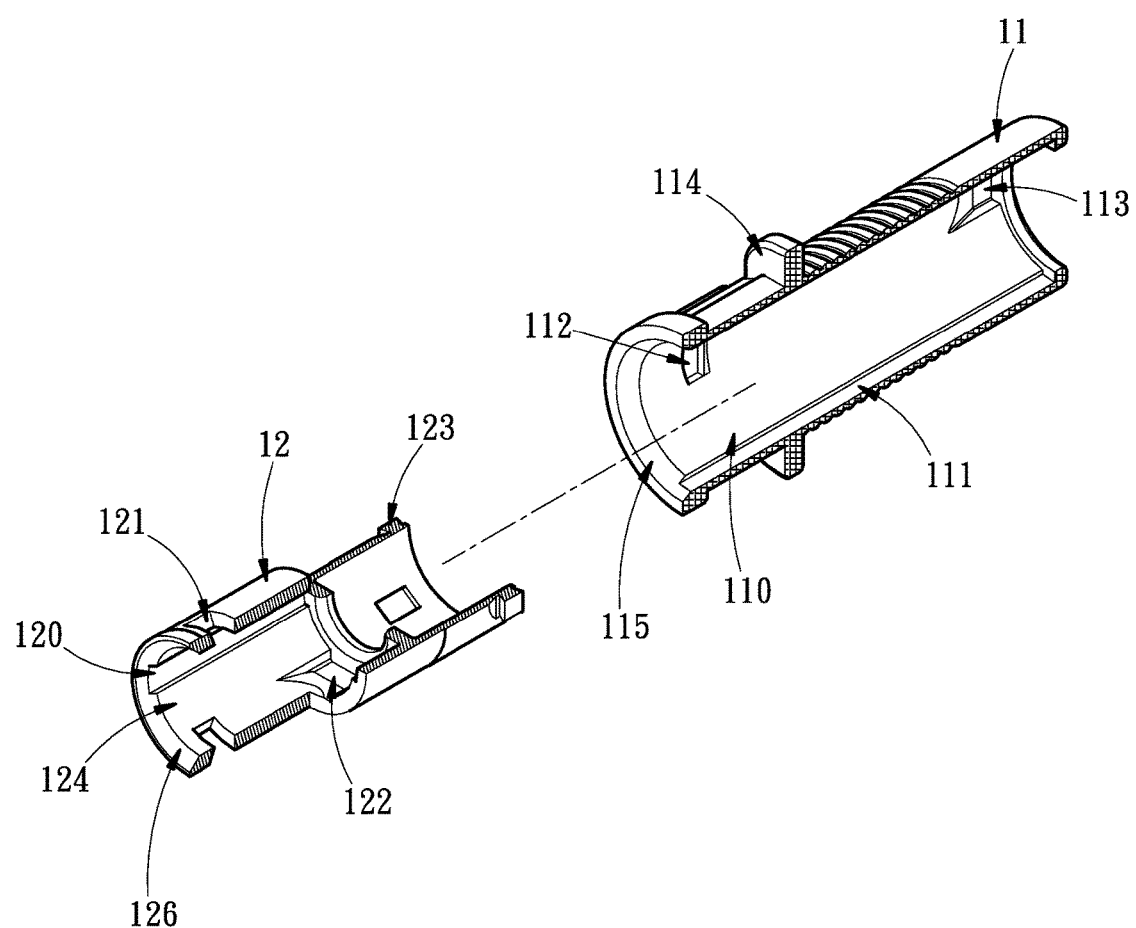
FIG. 6 is a schematic view of a second sleeve and a first sleeve of a needle head structure of a safety syringe in accordance with the present invention.
Figure 7A:
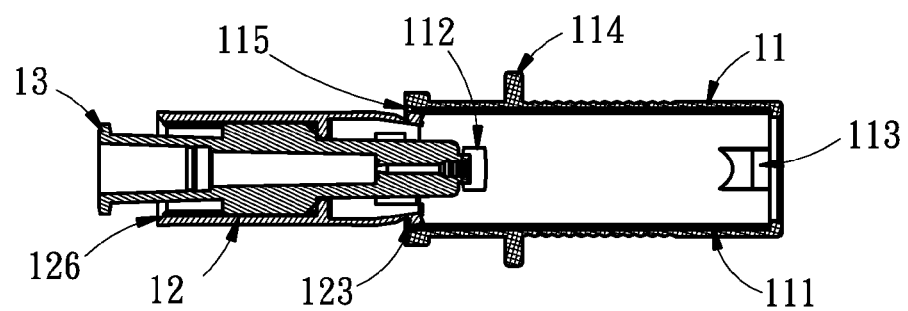
FIGS. 7a~7d are front views of installing a second sleeve and a first sleeve of a needle head structure of a safety syringe in accordance with the present invention.
Figure 7B:
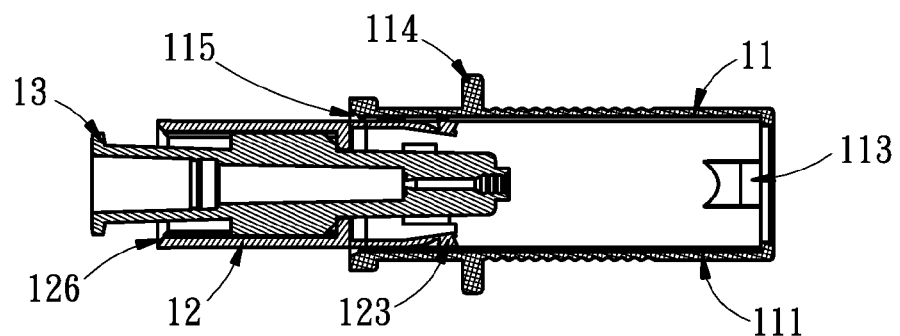
Figure 7C:
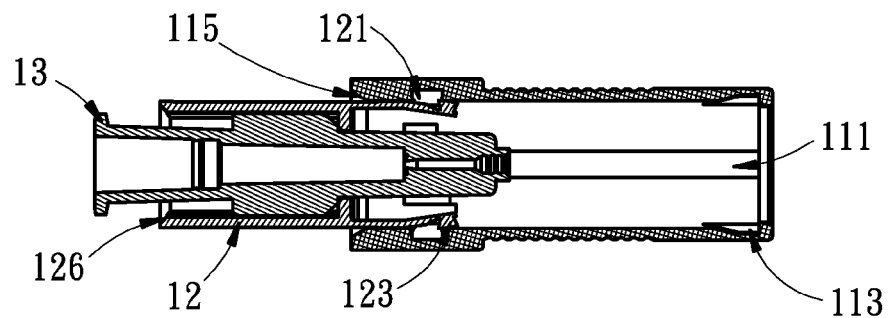
Figure 7D:
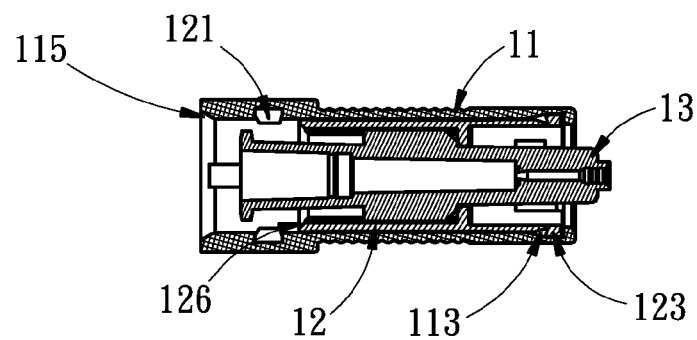
Figure 7E:
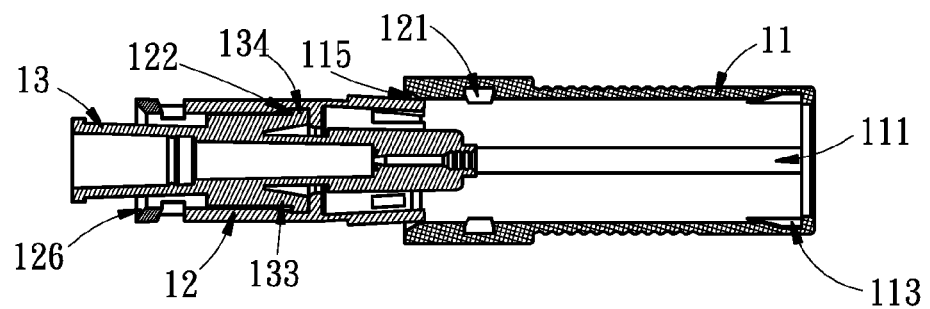
FIGS. 7e~7h are top views of installing a second sleeve and a first sleeve of a needle head structure of a safety syringe in accordance with the present invention.
Figure 7F:
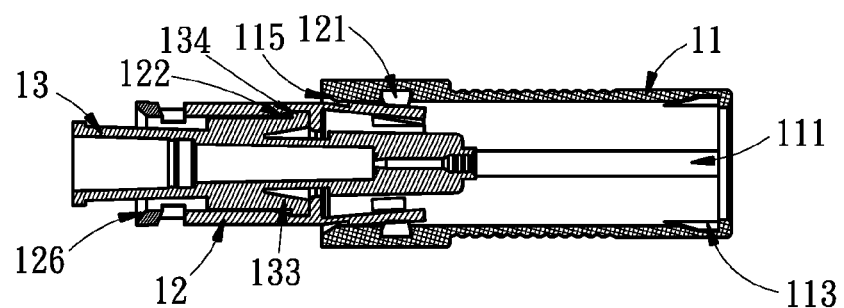
Figure 7G:
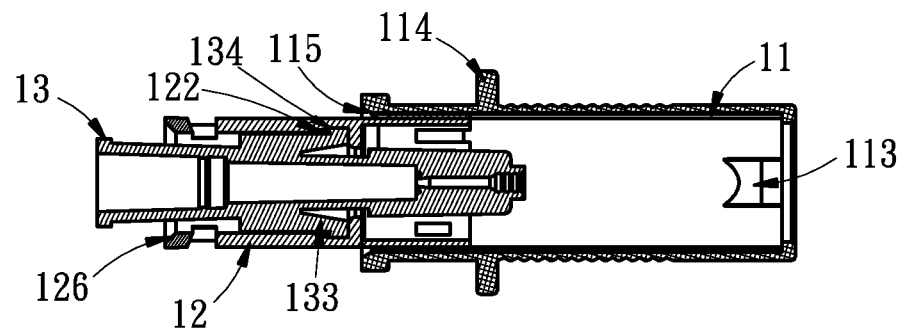
Figure 7H:
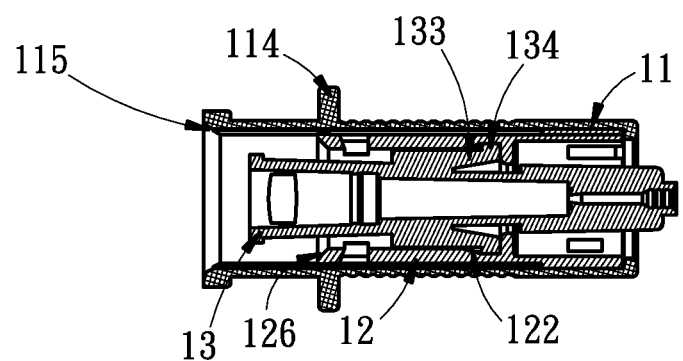
Figure 8:
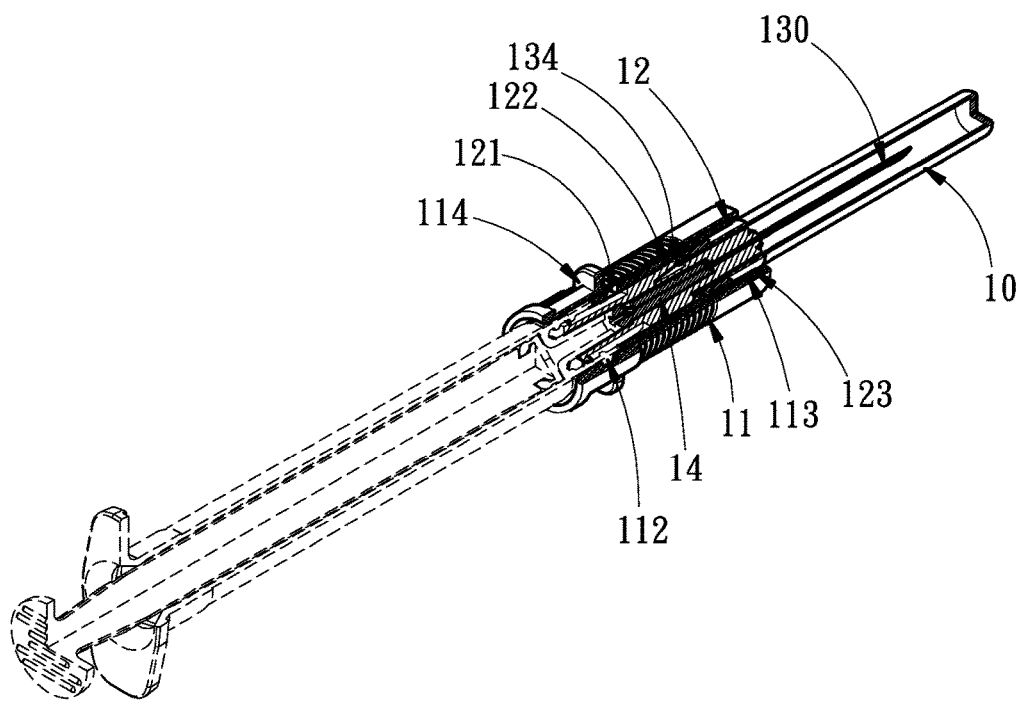
FIG. 8 is a schematic view of a needle head structure and a safety syringe in accordance with the present invention.

In FIGS. 4 and 5a~5h, the external periphery of the syringe holder 13 includes a latch plate 133 having the embedding protrusion 134 and a positioning portion 132, and the containing portion 124 at an end of the second sleeve 12 has a guide portion 120, latch portion 121, and groove 122 formed therein. When the syringe holder 13 and the second sleeve 12 are embedded and coupled to each other, the latch plate 133 of the syringe holder 13 enters from the embedding protrusion 134 and an aslant guide surface 126 of the second sleeve 12, so that the latch plate 133 is squeezed by the internal peripheral wall and pressed towards the center. Since the second sleeve 12 is made of plastic, therefore the second sleeve 12 has an appropriate deformation margin. When the syringe holder 13 penetrates deeply towards the front, the embedding protrusion 134 is passed through the latch portion 121 of the second sleeve 12, so that a position a is spread open slightly towards the outside (as shown in FIG. 5f), and then the syringe holder 13 is rotated to a side, and slid further towards the front after the positioning portion 132 is configured to be corresponsive to the guide portion 120, and the embedding protrusion 134 is configured to be corresponsive to the groove 122 to fix the second sleeve 12 to the syringe holder 13.

In FIGS. 6, 7a~7h and 8, an end of the second sleeve 12 has a positioning portion 125 and an embedding protrusion 123, and the containing portion 110 of the first sleeve 11 has a guide portion 111, a latch portion 112 and a groove 113. When the second sleeve 12 and the first sleeve 11 are embedded and coupled to each other, the embedding protrusion 123 of the second sleeve 12 enters from an aslant guide surface 115 at an end of the first sleeve 11 into the containing portion 110. Since the second sleeve 12 is made of plastic with an appropriate deformation margin, the embedding protrusion 123 is comprised towards the center and contracted. After the embedding protrusion 123 passes through the latch portion 112 of the first sleeve 11, the second sleeve 12 is rotated to a side, so that the positioning portion 125 falls into the guide portion 111, and then the second sleeve 12 is penetrated deeply towards the front, so that the embedding protrusion 123 falls into the groove 113 to fix the first sleeve 11 to the second sleeve 12.

The plunger 14, second sleeve 12, first sleeve 11 and protecting cover 10 are sheathed on the syringe holder 13 to form a safety syringe 1, and the containing portion 131 at an end of the syringe holder 13 of the safety syringe 1 is provided for coupling various different types of syringes.

Figure 9:
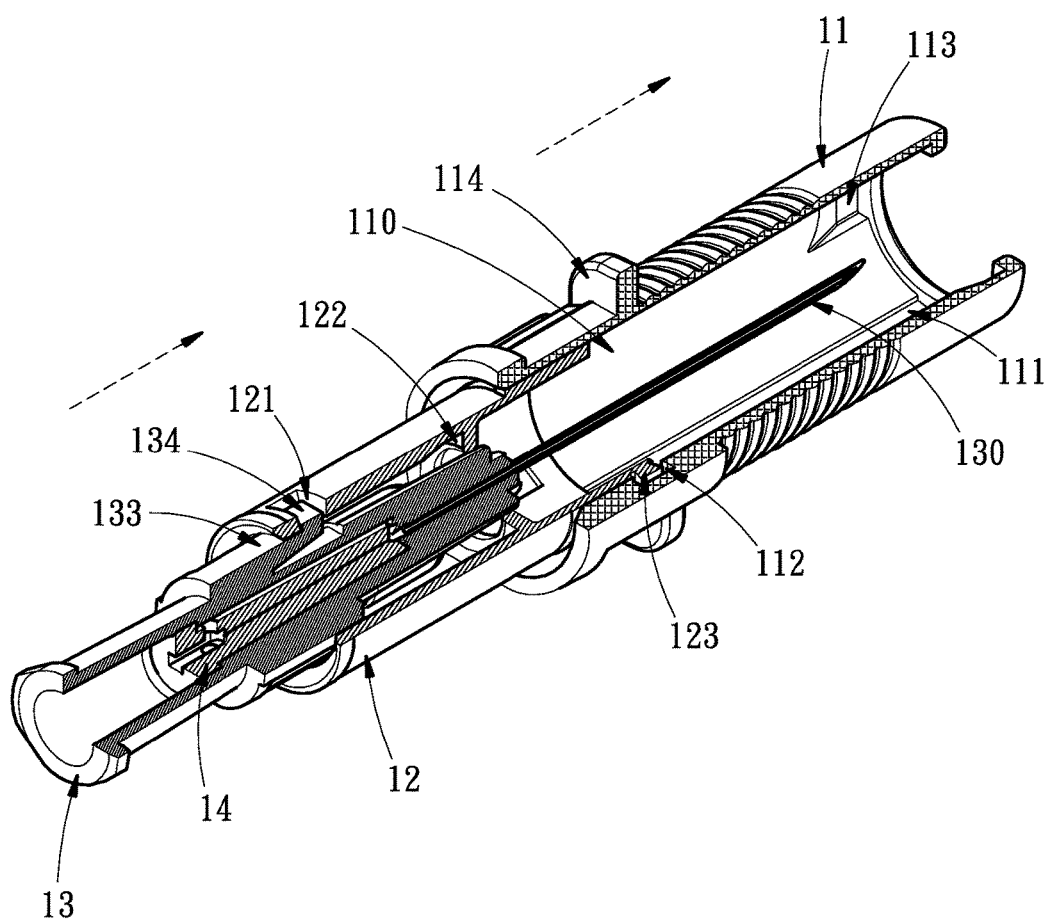
FIG. 9 is a schematic view of linking a needle head structure of a safety syringe in accordance with a preferred embodiment of the present invention.

In FIG. 9, after use of the safety syringe 1 of the embodiment of the present invention, the syringe body can be covered and protected completely. The first sleeve 11 and second sleeve 12 are stacked and embedded to the syringe holder 13. After use, the holding portion 114 of the first sleeve 11 may be held by a user's hand and pulled towards the syringe body 130 to separate the embedding protrusion 123 of the second sleeve 12 from the groove 113 of the first sleeve 11 and fall in and fixed into the latch portion 112 of the first sleeve 11. After the first sleeve 11 and the second sleeve 12 are fixed with each other, the sleeves are pulled towards the syringe body 130, so that the latch plate 133 of the syringe holder 13 having the embedding protrusion 134 is separated from the groove 122 of the second sleeve 12, and fall into the latch portion 121 of the second sleeve 12, and the second sleeve 12 is fixed to the syringe holder 13, and the distance from the first sleeve 11 to the second sleeve 12 can cover the syringe body 130 for protecting the syringe body 130, preventing the users from being pierced by the needle accidentally, as well as providing a convenient operation.

What is claimed is:

1. A needle head structure of a safety syringe, comprising:
a protecting cover, a first sleeve, a second sleeve, a syringe holder, and a plunger, wherein:
the protecting cover has an opening formed at an end of the protecting cover;
the first sleeve is a tubular body with an opening formed respectively at both ends of the first sleeve and a first containing portion formed therein for accepting the second sleeve, the first containing portion containing a first guide portion, a first groove and a first latch portion formed therein;
the second sleeve is a tubular body with an opening respectively formed at both ends of the second sleeve and a second containing portion formed therein for accepting the syringe holder, the second containing portion containing a second guide portion, a second groove and a second latch portion formed therein;
wherein an embedding protrusion is formed at an end of the second sleeve and configured to pass through the first groove and first latch portion of the first sleeve;

the syringe holder is a tubular holder, configured to engage the protecting cover, having a third containing portion disposed at an end of the syringe holder configured to accept the plunger, and a syringe body disposed at another end of the syringe holder, a positioning portion and a latch plate being formed on a periphery of the syringe holder, the latch plate configured to pass through the second groove and the second latch portion of the second sleeve;

the plunger includes an injecting portion, a diversion hole and a diversion portion; and wherein the first and second sleeves are disposed around the syringe holder, the plunger includes a guide channel, and when the first sleeve is pulled towards the syringe body, the embedding protrusion engages the first latch portion, the latch plate engages the second latch portion, and the first sleeve and the second sleeve completely cover the syringe body.

2. The needle head structure of a safety syringe according to claim 1, wherein the positioning portion of the syringe holder is configured to correspond to the second groove and the second latch portion of the second sleeve.

3. The needle head structure of a safety syringe according to claim 1, wherein the embedding protrusion of the second sleeve is configured to correspond to the first groove and the first latch portion of the first sleeve.

4. The needle head structure of a safety syringe according to claim 1, wherein the positioning portion of the syringe holder is configured to correspond to the second guide portion of the second sleeve.

5. The needle head structure of a safety syringe according to claim 1, wherein the embedding protrusion of the second sleeve is configured to correspond to the first guide portion of the first sleeve.

6. The needle head structure of a safety syringe according to claim 1, wherein when the second sleeve and the first sleeve are coupled to each other, the embedding protrusion of the second sleeve enters from an end of the first sleeve into the first containing portion via an angled guide surface of the first sleeve, so that the embedding protrusion is squeezed inwards, and when the embedding protrusion passes through the first latch portion of the first sleeve and the second sleeve is rotated the embedding protrusion falls into the first guide portion, and the embedding protrusion falls into the first groove, so as to fix the first sleeve to the second sleeve.

7. The needle head structure of a safety syringe according to claim 1, wherein when the syringe holder and the second sleeve are coupled to each other, the latch plate of the syringe holder is configured to be squeezed by an internal peripheral wall of the second sleeve, and when the latch plate passes through the second latch portion of the second sleeve and then the syringe holder is rotated so that the latch plate falls into the second guide portion and then advances into the second groove to fix the second sleeve to the syringe holder.

* * * * *